US006675415B2

(12) United States Patent
Wong

(10) Patent No.: US 6,675,415 B2
(45) Date of Patent: Jan. 13, 2004

(54) X-RAY TRANSPARENT HOSPITAL BED COMPATIBLE WITH OPEN GEOMETRY PORTABLE CT SCANNERS

(75) Inventor: John W. Wong, Bloomfield Hills, MI (US)

(73) Assignee: William Beaumont Hospital, Royal Oaks, MI (US)

(*) Notice: Subject to any disclaimer, the term of this patent is extended or adjusted under 35 U.S.C. 154(b) by 0 days.

(21) Appl. No.: 10/340,346

(22) Filed: Jan. 10, 2003

(65) Prior Publication Data

US 2003/0101513 A1 Jun. 5, 2003

Related U.S. Application Data

(63) Continuation of application No. 09/821,004, filed on Mar. 29, 2001, now Pat. No. 6,526,609.

(51) Int. Cl.[7] ................................................. A47B 7/00
(52) U.S. Cl. .................... 5/601; 5/613; 5/942; 378/209
(58) Field of Search .......................... 5/601, 613, 942, 5/600; 378/209, 195

(56) References Cited

U.S. PATENT DOCUMENTS

| | | | |
|---|---|---|---|
| 2,454,802 A | 11/1948 | Hipps |
| 3,947,686 A | 3/1976 | Cooper et al. |
| 4,030,719 A | 6/1977 | Gabriele et al. |
| 4,110,856 A | 9/1978 | Benoit et al. |
| 4,345,344 A | 8/1982 | Gadoury et al. |
| 4,387,888 A | 6/1983 | Marinakis |
| 4,568,071 A | 2/1986 | Rice |
| 4,665,574 A | 5/1987 | Filips et al. |
| 4,669,136 A | 6/1987 | Waters et al. |
| 4,688,278 A | 8/1987 | Van Aspert |
| 4,926,457 A | 5/1990 | Poehner et al. |
| 4,985,946 A | 1/1991 | Foster et al. |
| 5,077,843 A | 1/1992 | Foster et al. |
| 5,083,332 A | 1/1992 | Foster et al. |
| 5,111,540 A | 5/1992 | Caya |
| 5,134,737 A | 8/1992 | Wyman |
| 5,179,744 A | 1/1993 | Foster et al. |
| 5,197,474 A | 3/1993 | Englund et al. |
| 5,272,776 A | 12/1993 | Kitamura |
| 5,377,370 A | 1/1995 | Foster et al. |
| 5,513,406 A | 5/1996 | Foster et al. |
| 5,566,409 A | 10/1996 | Klearman |
| 5,590,429 A | 1/1997 | Boomgaarden et al. |
| 5,613,254 A | 3/1997 | Clayman et al. |
| 5,745,936 A | 5/1998 | Van McCutchen et al. |
| 5,790,996 A | 8/1998 | Narfstrom |
| 5,836,027 A | 11/1998 | Leventhal et al. |
| 5,987,672 A | 11/1999 | Oosterwaal |
| 6,003,174 A | 12/1999 | Kantrowitz et al. |
| 6,070,281 A | 6/2000 | Reich |
| 6,073,291 A | 6/2000 | Davis |
| 6,092,248 A | 7/2000 | Boemmel et al. |
| 6,094,760 A | 8/2000 | Nonaka et al. |
| 6,104,780 A | 8/2000 | Hanover et al. |
| 6,131,690 A | 10/2000 | Galando et al. |

Primary Examiner—Robert J. Sandy
Assistant Examiner—Katherine Mitchell
(74) Attorney, Agent, or Firm—Brinks Hofer Gilson & Lione

(57) ABSTRACT

A hospital bed adapted for use with an open geometry imaging system, such as a C-arm imager, is provided. The hospital bed includes a mobile base, a frame, a bed top, and a patient support. At least one portion of the bed top and patient support are substantially radiotransparent. The radiotransparent portions are capable of axial displacement along the lengthwise axis of the bed, thereby allowing the use of an imager on a patient in the bed without interference from the base. The axial displacement is preferably indexed to at least one predetermined stop position. One or more independent lateral sections can be selectively moved away from the radiotransparent portion, allowing for a reduction in the overall width of the bed. A patient transport system is also provided, in which the bed top and attached patient support can be used as a portable support, such as a stretcher, and may be secured to the base for subsequent transport and/or imaging when appropriate.

5 Claims, 10 Drawing Sheets

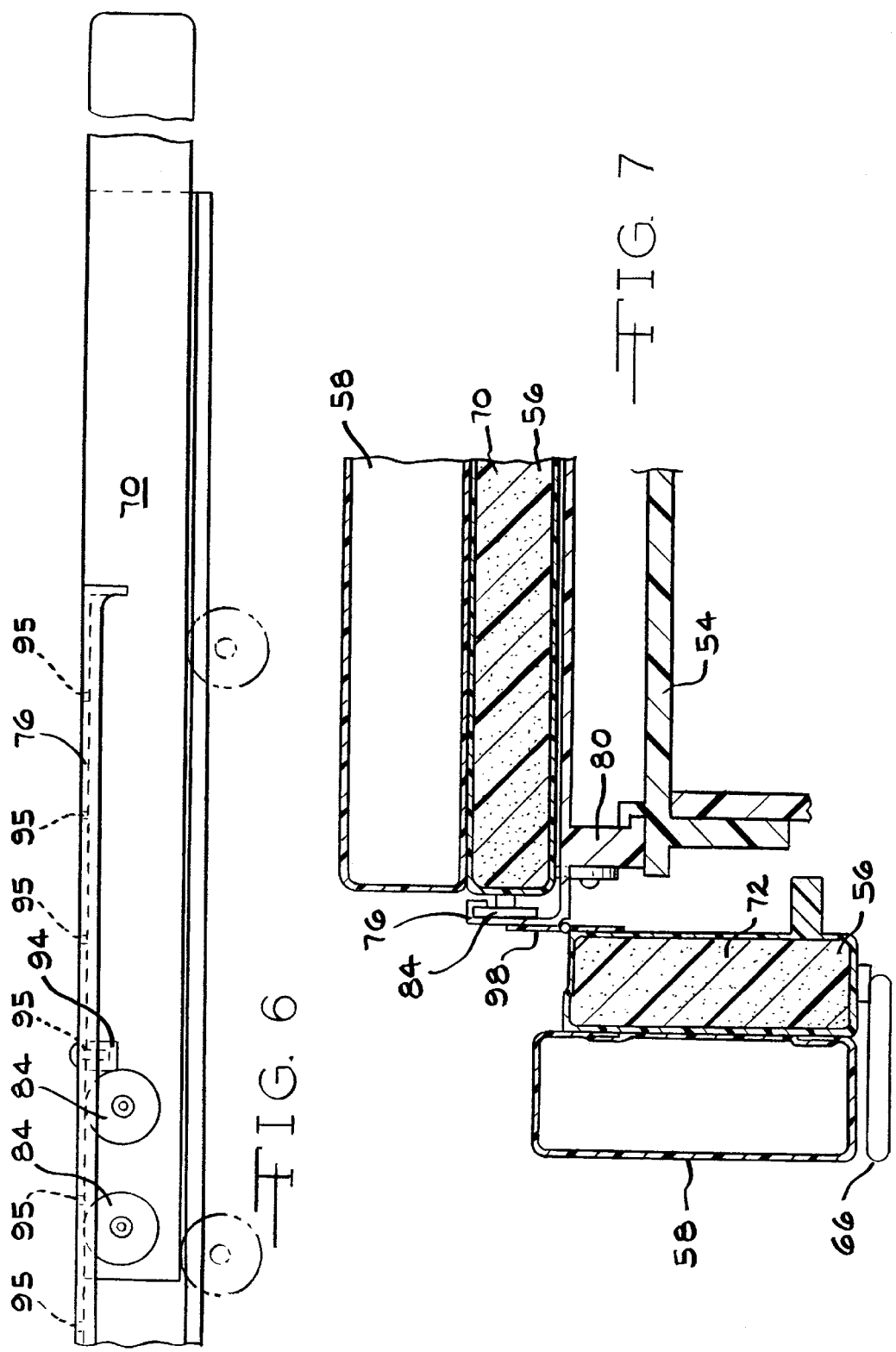

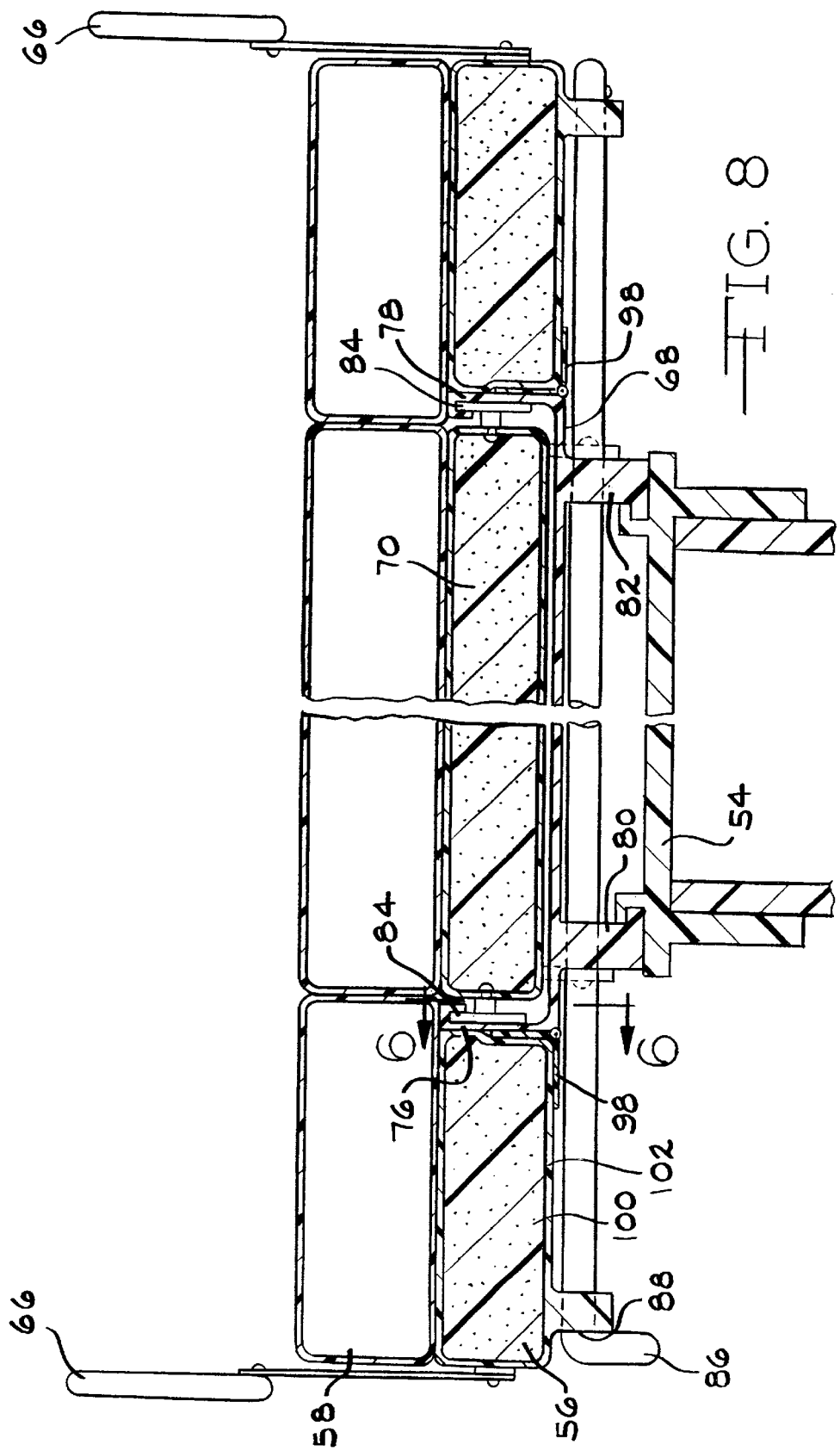

X-RAY TRANSPARENT HOSPITAL BED COMPATIBLE WITH OPEN GEOMETRY PORTABLE CT SCANNERS

This application is a continuation of application Ser. No. 09/821,004, filed Mar. 29, 2001, now U.S. Pat. No. 6,526,609 which is hereby incorporated by reference herein.

FIELD OF THE INVENTION

The present invention relates to hospital beds and patient support systems. More specifically, the present invention relates to hospital beds and patient support systems adapted for use with open geometry imaging systems.

BACKGROUND OF THE INVENTION

Hospitals and other patient care facilities often dedicate rooms to house imaging systems. The systems are typically fixed in space and require movement of the patient to the dedicated room for each imaging procedure. Also, the imaging system often contains a couch or other surface that supports the patient during the imaging procedure. This arrangement requires transferring the patient from a hospital bed to the fixed support of the imaging system.

Recent advances in imaging technology have allowed for the development of mobile, open geometry imaging systems such as mobile CT and fluoroscopy imaging units. Mobile C-arm imaging units provide examples of these systems. A C-arm imaging system is a real-time fluoroscope frequently used to image a patient's chest or head areas. The imaging system derives its name from the arcuate main arm that supports the imaging components. An x-ray tube is positioned at one end of the arm, and an image receiver is positioned at the opposite end of the arm. The unit does not contain an integrated patient support. Rather, the entire imaging apparatus is mounted on a mobile base which allows the imager to be moved to the patient for imaging procedures.

Some mobile C-arm units contain a single C-arm and have imaging components that are relatively small compared to the size of the C-arm This arrangement facilitates movement of the mobile system. U.S. Pat. No. 6,131,690 to Galando et al. for a MOTORIZED SUPPORT FOR IMAGING MEANS provides an example of this type of unit. Other units, however, contain multiple C-arms and/or have bulky imaging components. While these units are mobile, the complex configurations of these units can make it difficult to navigate the imagers around obstacles, such as hospital beds. U.S. Pat. No. 6,104,780 to Hanover, et al. for a MOBILE BI-PLANAR FLUOROSCOPIC IMAGING APPARATUS provides an example of this type of unit.

A major advantage provided by mobile imaging systems is the ability to bring the imager to the patient, rather than the opposite arrangement, which is the case with traditional imaging equipment. This requires that some type of patient support be available for use with the mobile imager. Adding a patient support to a mobile unit may, however, hinder its mobility. Consequently, hospital beds that allow positioning of mobile imaging systems around the bed for easy access to the patient during imaging procedures will be necessary for the successful integration of mobile imaging systems into hospitals and other patient care facilities Such hospital beds will further the modern trend of keeping patients on a single support throughout a stay in the patient care facility. Further, such beds will increase the overall efficiency of patient care. Ideally, the new hospital beds will retain all of the benefits of traditional hospital beds while allowing the desired access by a variety of mobile imaging systems, including those that incorporate multiple C-arms and bulky imaging components.

There have been previous attempts to provide a hospital bed that solve the problems mentioned-above. U.S. Pat. No. 4,985,946 to Foster et al. for a HOSPITAL BED ADAPTED FOR USE WITH A C-ARM is exemplary of these attempts. The structure disclosed in this reference still requires navigation of the mobile C-arm unit about the base of the hospital bed. In addition, the Y-shaped base of the hospital bed may not accommodate some of the larger and bulkier C-arm units, such as the apparatus taught by Hanover, et al. Also, when the simultaneous use of multiple C-arm or other imaging units is necessary or desired for a single imaging procedure, the bed disclosed by Foster et al. will preclude such arrangements. Furthermore, the structure of the hospital bed taught by Foster et al. may lead to imaging artifacts because the base of the bed remains near the patient support surface and imaging components during operation of the imaging system.

SUMMARY OF THE INVENTION

The present invention provides a hospital bed and patient support system that are adapted for use with mobile open geometry imaging systems. In part, the invention provides a bed that can be used as the main patient support during a stay in a patient care facility. The bed retains the benefits of traditional hospital beds, such as comfort to the patient, the ability to select among multiple positions, and features for ensuring retention of the patient in the bed.

The invention also provides adaptations making the bed and support system compatible with open geometry imaging systems, especially mobile C-arm imaging units. In this sense, compatibility primarily refers to two features of the invention. First, the bed and support system are able to position a patient such that the bed or support system does not prohibit access by the imaging unit. Second, the bed and patient support system include a surface that is substantially radiotransparent, ensuring that the bed or support system does not interfere with the imaging process.

In one preferred embodiment, a hospital bed according to the present invention comprises a mobile base, a bed frame, an elongated bed top supported by the frame, and a patient support disposed on the bed top. The bed top has a main section and at least one lateral section. The main section is capable of axial displacement between an initial position and at least one extended position along its lengthwise axis. The lateral section is capable of selective movement away from the main section, which allows for a selective reduction of the width of the bed. The patient support has a first portion similar in shape to the main section of the bed top and at least one second portion similar in shape to the lateral section. At least the bed top and patient support are comprised of substantially radiotransparent materials.

In a second preferred embodiment, a patient support system is provided. The patient support system is similar to the hospital bed in the sense that it retains features of traditional hospital beds, has substantially radiotransparent components, and is adapted for use with mobile imaging systems. In the patient support system, however, the bed top and patient support are detachable from the bed frame. In this manner, the base and frame effectively serve as a docking station for the bed top and patient support. Thus, the bed top and patient support can be used to support a patient independent of the remainder of the bed. In one application, the bed top and patient support can be used as a stretcher in a critical care vehicle. When necessary or desired, the stretcher can be secured to the frame, thereby placing the patient on a complete hospital bed.

While the present invention is particularly well adapted for use with mobile, open geometry imaging systems, it will be appreciated that the invention is not limited to this particular application.

BRIEF DESCRIPTION OF THE DRAWINGS

FIG. 6 is a schematic view of structural features of the bed top that allow indexing of the axial displacement of the main section.

FIG. 7 is a perspective view of a bed top and patient support surface in accordance with the present invention showing lateral portions of the bed top and patient support surface in a lowered position.

FIG. 8 is a cross-sectional view of a bed top and patient support surface of a hospital bed in accordance with the present invention

DETAILED DESCRIPTION OF THE PREFERRED EMBODIMENTS OF THE INVENTION

Figure 1:
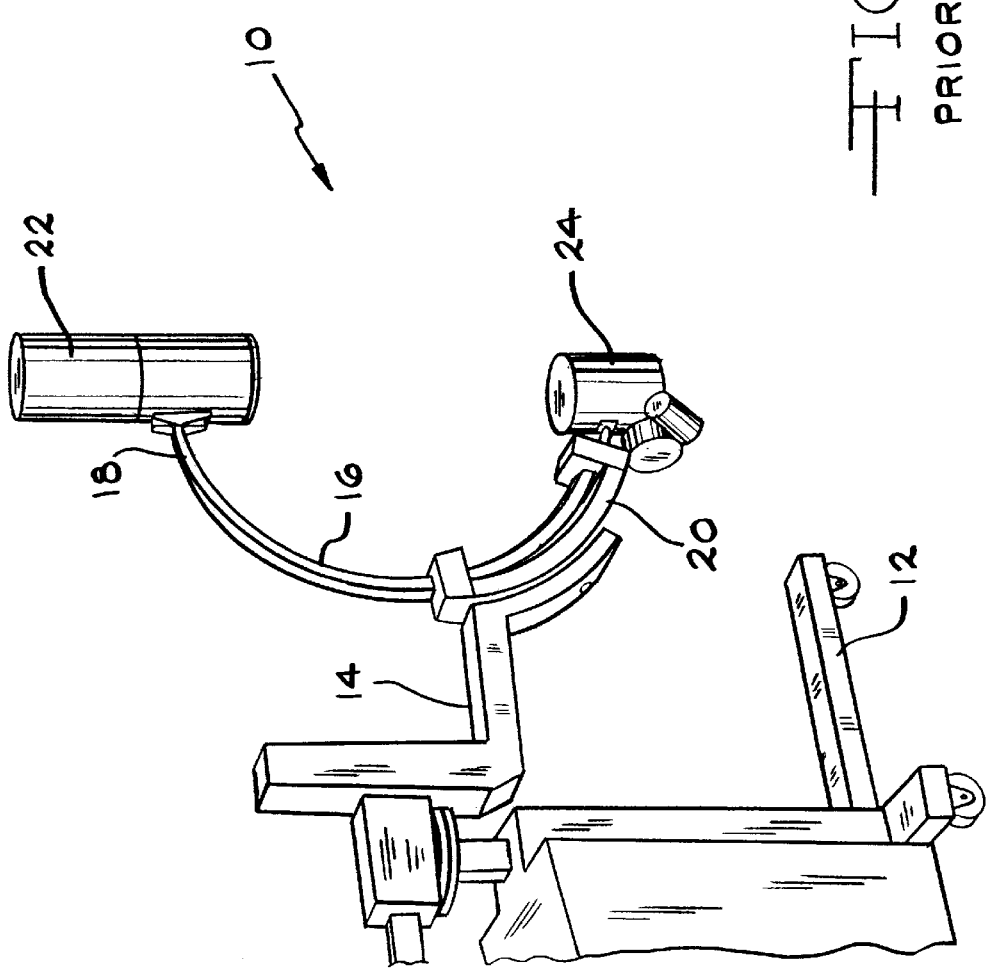
FIG. 1 is a perspective view of a mobile C-arm imaging system having a single C-arm.
Figure 2:
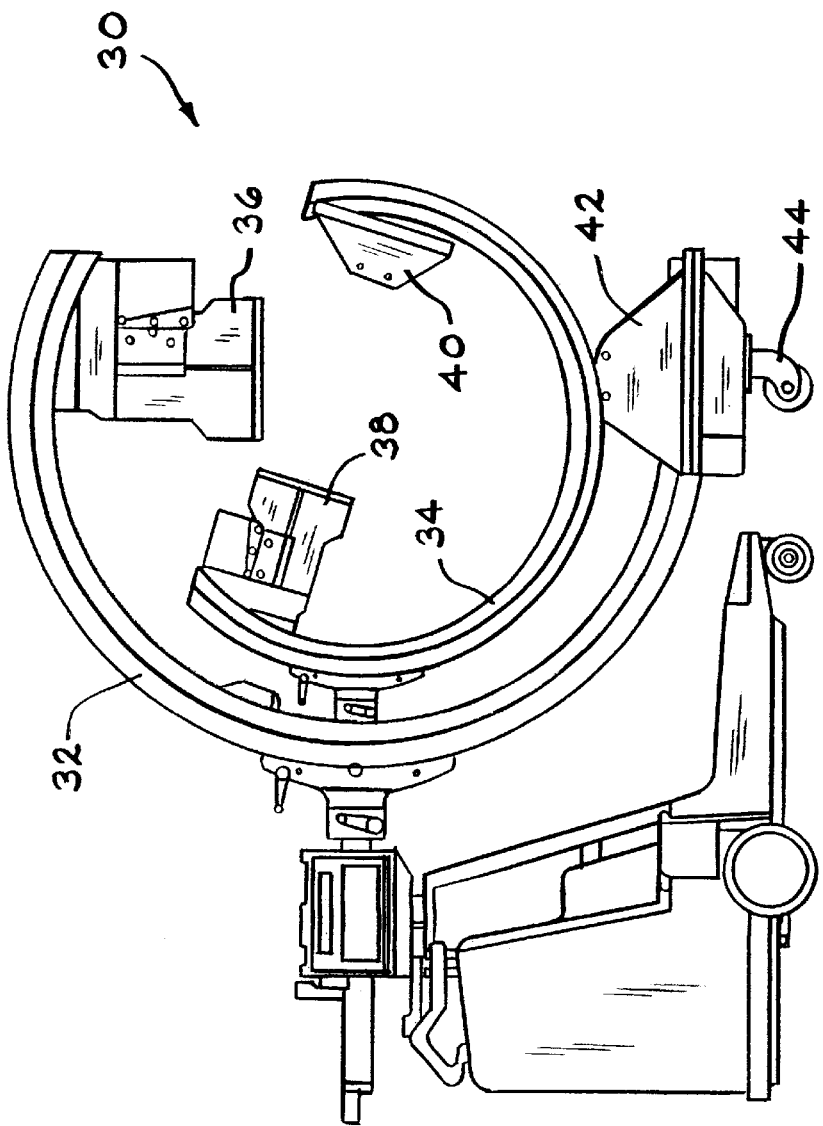
FIG. 2 is a perspective view of a mobile C-arm imaging system having multiple C-arms.

To fully describe the features of the present invention, it is helpful to first consider examples of mobile open geometry imaging systems with which beds and support systems according to the present invention can be utilized. FIGS. 1 and 2 illustrate two examples of mobile C-arm imaging systems. FIG. 1 illustrates a relatively simple mobile C-arm unit 10. The unit 10 has a mobile base 12, and outwardly extending support 14, and a C-arm 16. The C-arm 16 generally resembles the shape of the letter C, but may have any arcuate shape. The C-arm 16 has first 18 and second 20 ends positioned opposite each other. An x-ray source 22 is positioned on the first end 18 and an image receiver and/or intensifier 24 is positioned on the second end 20. In this arrangement, the receiver and/or intensifier 24 is positioned directly opposite the x-ray source 22. As shown in FIG. 1, the x-ray source 22 is typically positioned on the first 18, or upper, end with the receiver and/or intensifier 24 positioned on the second 20, or lower, end. In this configuration, the x-ray source 22 directs x-rays downward toward the patient during an imaging procedure. Of course, the x-ray source 22 and receiver and/or intensifier 24 can be reversed in position.

FIG. 2 presents a mobile C-arm unit 30 having a relatively complex configuration. The unit 30 includes first 32 and second 34 C-arms, first 36 and second 38 x-ray sources, and first 40 and second 42 image receivers and/or intensifiers. The second C-arm 34 is nestably disposed within the first C-arm 32. To accommodate this configuration, the first C-arm 32 is typically larger in size than the C-arm of the unit shown in FIG. 1. Due to various factors, including the relatively large size of the first C-arm 32, the inclusion of a second C-arm 34, and the use of relatively large imaging components, the C-arm unit 30 can be quite cumbersome. To provide additional support, the unit 30 may also contain supports 44 for resting the first C-arm 32 on the floor.

Figure 3:
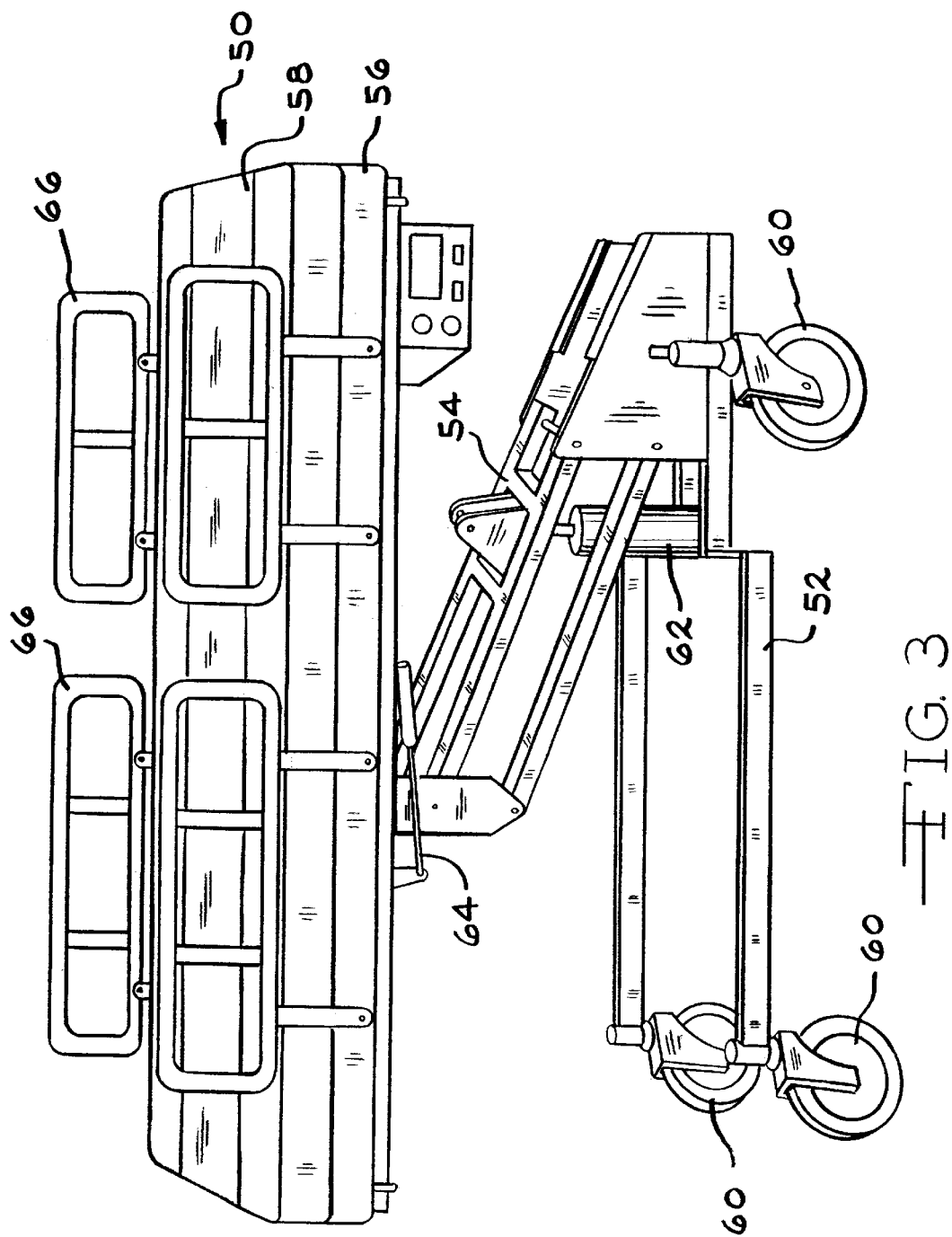
FIG. 3 is a perspective view of a hospital bed in accordance with the present invention.

FIG. 3 illustrates a first preferred embodiment of the present invention. In this embodiment, a hospital bed 50 includes a base 52, a bed frame 54, a bed top 56, and a patient support 58. Preferably, the base 52 includes wheels or casters 60 that facilitate movement of the bed 50. The hospital bed 50 also, preferably includes several features common to hospital beds in general, such as at least one hydraulic arm 62 or other conventional means for adjusting the height of the bed top 56 and patient support surface 58 relative to the base 52 and floor, a lever 64 or other means for controlling such adjustment, and side rails 66 for retaining a patient on the patient support surface.

Figure 4:
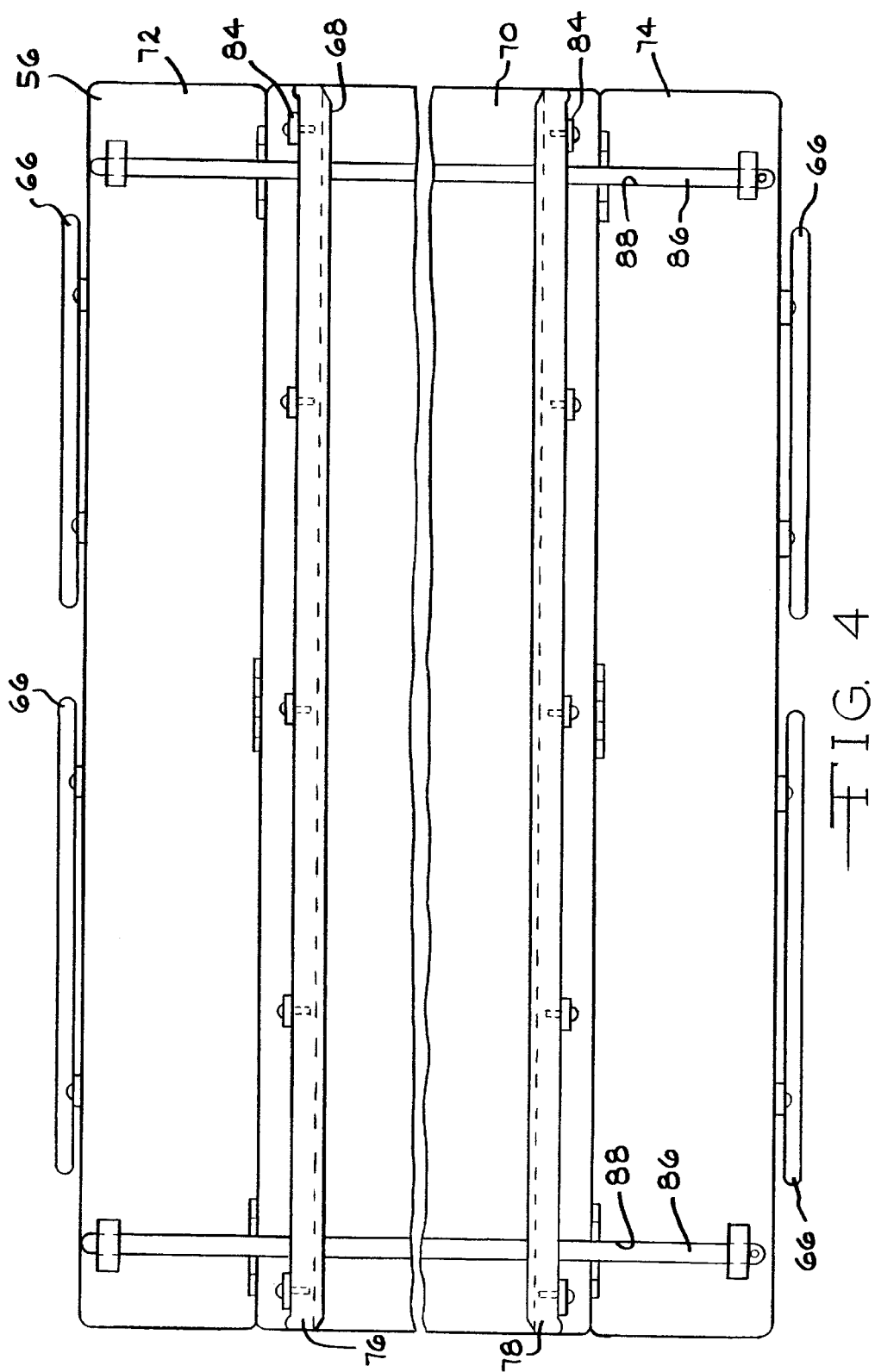
FIG. 4 is a perspective view, partially broken away, of a bed top and patient support surface in accordance with the present invention.

The bed top 56 provides a flat surface that rests on the bed frame 54. The bed top 56 provides support to the patient support surface 58. FIG. 4 illustrates the bed top 56 as viewed from below the bed 50. The bed top 56 preferably comprises a frame 68 defining structural members for attaching the bed top 56 to the bed frame 54, and at least two independent sections, a main section 70 and at least one lateral section 72. Preferably, the bed top 56 includes a second lateral section 74. FIG. 4 illustrates a preferred embodiment of the bed top 56. The bed top preferably defines a main support having first 76 and second 78 rails. The frame 68 defines first 80 and second 82 cleats that provide a surface for securing the rails of the bed top 56 to the bed frame 54.

The first lateral section 72 sits adjacent the first rail 76 and the second lateral section 74 sits adjacent the second rail 78. In this embodiment, the main section 70 is preferably wide enough to support an average-sized patient and extends the entire length of the bed top 56. Also preferable, the lateral sections 72, 74 are preferably equal in size, each extending the entire length of the bed top 56. Of course, the main 70 and lateral sections 72, 74 can be arranged in any manner relative to each other and the bed top. Furthermore, the main 70 and lateral sections 72, 74 can each have any dimensional shape that achieve the purposes of the present invention.

Preferably, the main 70 and lateral sections 72, 74 are independent of each other and the bed frame 54. As will be developed more fully below, the main section 70 is capable of displacement along the lengthwise axis of the bed 50, and the lateral sections 72, 74 are capable of selectively moving away from the main section 70. The independence of these sections allows such movements.

Preferably, the bed top 56 is horizontally segmentable in at least one position along its length such that the bed top 56 can be alternated between various positions. Due to the independent connection of the main 70 and lateral sections 72. 74 to the bed frame 54, each position at which the bed top 56 is segmentable preferably comprises a hinge or other bending means on the rails 76, 78, and the main 70 and lateral 72, 74 sections.

Figure 5:
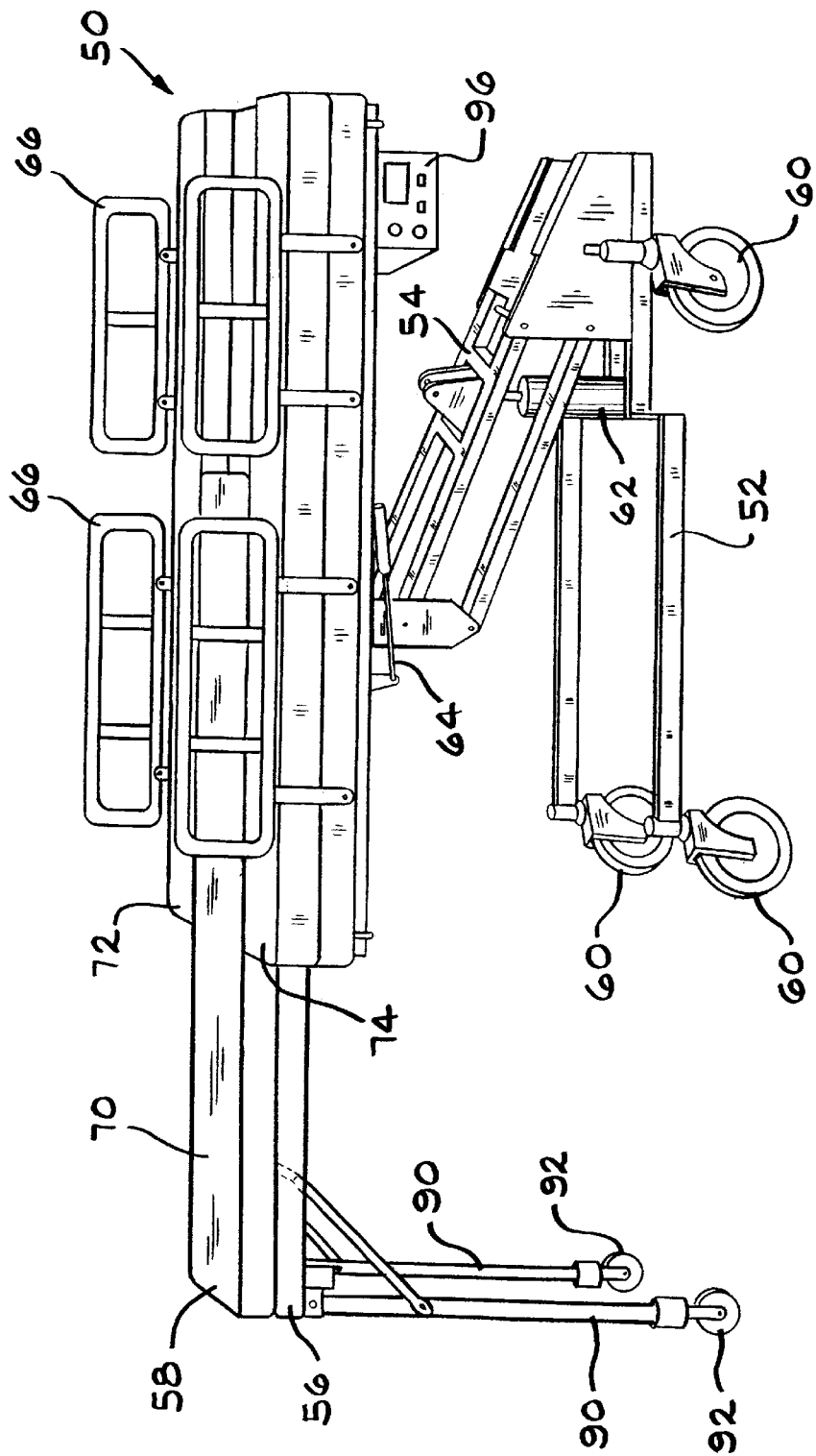
FIG. 5 is a perspective view of a hospital bed in accordance with the present invention showing the bed top and patient support surface in an extended position.

The main section 70 of the bed top 56 is capable of axial displacement along its lengthwise axis, independent of the lateral sections 72, 74. This allows the main section 70 of the bed top 56 to be moved away from the remainder of the bed top 56, i.e., the lateral sections 72, 74, and extended away from the base 52 of the bed 50. That is, the axial displacement allows the main section 70 to be moved from an initial position to an extended position. In the initial position, the main section 70 is preferably aligned with the lateral sections 72, 74 of the bed top 56 relative to the lengthwise axis of the bed top 56. As will be developed more fully below, the extended position preferably places at least a portion of the main section 70 at a distance from the remainder of the bed top 56 and bed 50. FIG. 5 illustrates the bed top 56 in an extended position. The extended position can be one or more predetermined stop positions, as will be developed more fully below, or may be any position along the lengthwise axis of the bed top 56.

The axial displacement of the main section is preferably accomplished by a slideable relationship between the main section 70 of the bed top 56 and the rails 76, 78. For example, the rails 76, 78 can define channels or grooves that receive a corresponding projection 84 that can include pins, wheels, bearing assemblies, or other rolling or sliding elements on the sides of the main section 70 of the bed top 56. FIG. 4 illustrates a preferred embodiment of the bed top 56. In this arrangement, the rails 76, 78 define channels having an opening directed toward the sides of the main section. Wheels or bearings 84 are attached to the sides of the main section 70, and are slideably received by each of the rails 76, 78. Also preferable, a pin 86 or other locking structure interacts with a recess 88 or other retaining feature to lock the main section 70 in a stationary position, i.e., prevent axial displacement.

The axial displacement of the main section 70 can be accomplished with the assistance of an electric motor, hydraulics, and/or fluidics, or can be manual in nature. Preferably, the main section of the bed top is able to be displaced a distance away from the bed frame equal to at least approximately one-third of the overall length of the bed top. Alternatively, the main section can be displaced along its entire length or along any other fraction of its length. The rails 76, 78 preferably define end plates that prevent displacement beyond the length of the bed top 56.

The hospital bed 50 according to the present invention may also contain additional features that assure stability of the bed 50 during axial displacement of the main section 70, of the bed top 56. For example, a counterweight may be disposed in or attached to the base 52 of the bed. Also, the base 52 main define pins, loops, or other structural features that cooperate with corresponding features on a floor or wall to retain the bed in a particular position. Furthermore, as illustrated in FIG. 5, one or more additional support projections 90 can be used to support the end of the main section 70 of the bed top 56 that moves away from the base 52 during axial displacement. The additional support projection 90 may comprise a permanently affixed leg that is capable of moving with the main section 70 during displacement. As illustrated in FIG. 5, the additional support projection 90 of this embodiment preferably includes a roller or caster 92 that allows easy movement of the additional support projection 90 during displacement Essentially any body known in the art that is capable of allowing the extra support projection 90 to move along a floor during axial displacement of the main section 70 with minimal friction can be used as the roller or caster 92. Alternatively, the additional support projection 90 may comprise a separate support member that can be attached to the main section 70 of the bed top 56 when necessary, such as when the main section 70 is in a displaced position. Furthermore, the extra support projection 90 need not have a roller or caster.

The axial displacement of the main section 70 of the bed top 56 is preferably indexed to one or more predefined positions. This indexing allows a user to easily select a particular predefined position as the extended position during axial displacement of the main section 70 of the bed top 56. The indexing can be accomplished in a variety of manners. For example, as illustrated in FIG. 6, the structural features of the bed top 56 main define one or more mechanical stops 94, such as projections, that serve to prevent the wheels 84 or other sliding and/or rolling elements of the main section 70 from moving further along its lengthwise axis unless the user bypasses the mechanical stop 94, such as by selectively removing the mechanical stop 94 or by navigating the wheels 84 or other sliding and/or rolling elements around the stop 94. Also, as shown in FIG. 5, a computer 96 or other programmable means can be attached to the bed 50 in a manner that allows the computer 96 to control the axial displacement of the main section 70 between the initial and extended positions. In this embodiment, a user, such as a health care provider, can program one or more extended positions based on distance, percent of bed length, percent of patient height, or any other calculation.

The predefined positions are preferably equal to common lengths associated with frequently performed imaging procedures. For example, one predefined position may allow the main section 70 of the bed top 56 to be displaced a length equal to approximately one-third of the total length of the bed top 56. This length would allow the main section 70 to be displaced a distance away from the frame 54 that is suitable for imaging procedures conducted on the head of the patient. Likewise, another predefined position may allow the main section 70 to be displaced ½ of its total length. This distance is useful for imaging procedures involving the chest of a patient.

Of course, any positions along the length of the bed top 56 can be used as the predefined positions. Furthermore, the structural features of the hospital bed 50 may allow a user to customize the predefined lengths according to his or her applications. For example, as illustrated in FIG. 6, a channel on the bed top 56 may allow a user to position a mechanical stop 94, such as a projection, within any of a number of recesses 95 along the length of the bed top 56, effectively defining one of the predefined positions at which the bed top 56 will stop during axial displacement. Also, as described above, a user can program the predefined positions into a computer 96 that controls the axial displacement of the main section 70.

As illustrated in FIG. 7, the lateral sections 72, 74 are preferably capable of selective movement away from the main section 70 of the bed top 56. This movement effectively allows the width of the bed 50 to be reduced. Preferably, this movement is accomplished by hinges 98 or other linkage or connection means attached to the rails 76, 78 or bed frame 54 and the lateral sections 72, 74 of the bed top 56.

The entire bed 50, including all components, is preferably comprised of substantially radiotransparent materials. Alternatively, at least a portion of the bed top 56 and patient support 58 are radiotransparent. This does not, however, require the entire bed 50 to be made from the same material. Rather, the different elements of the bed can be fabricated from different materials that are substantially radiotransparent and provide the desired characteristics of a particular element. For example, the base 52 and frame 54 need to comprise rigid bodies capable of withstanding the stress of supporting a patient over an extended period of time. Thus, a solid composite material, such as polycarbonate, can be used. Alternatively, any polymeric or fiber-based material capable of providing the desired rigidity and x-ray transparency can be used. As shown in FIG. 8, the bed top 56 is preferably comprised of a stiff foam inner core 100 encased in a carbon fiber shell 102.

Figure 9:
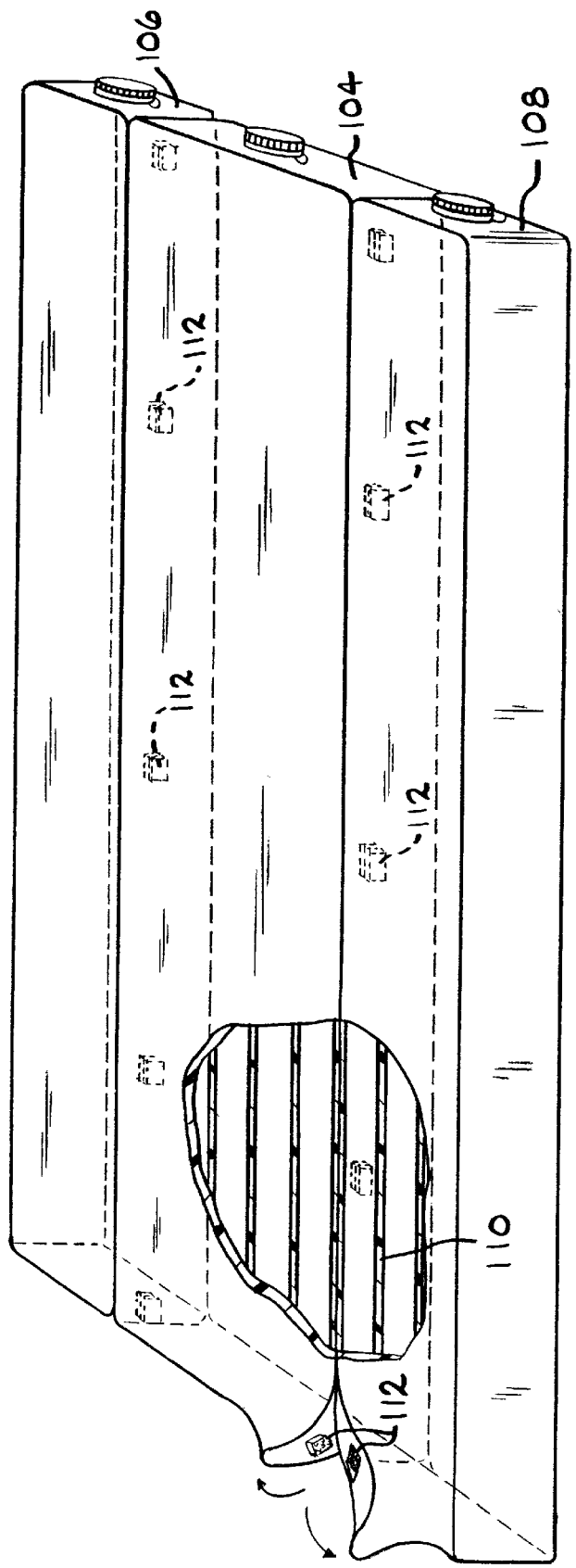
FIG. 9 is a peripheral view of an air mattress utilized for a patient support surface in accordance with the present invention.

The patient support surface 58 is also preferably comprised of a material that is substantially radiotransparent. For the patient support 58, the material chosen represents a balance between the need for comfort to the patient and radiotransparency. Preferably, the patient support 58 is a mattress comprising a puncture resistant material that defines one or more chambers capable of holding air or another gas. FIG. 9 illustrates an air mattress suitable for use in the present invention. The use of multiple chambers allows for controlled distribution of gas or air throughout the patient support, which can increase patient comfort and can also aid in positioning a patient during imaging procedures. More preferred is an air mattress that defines a plurality of independent chambers that individually correspond to the dimensions of the main and lateral sections of the bed top. Particularly preferred is an air mattress having a main chamber 104 that corresponds to the dimensions of the main section 70 of the bed top 56, and two lateral chambers 106, 108 that correspond to the dimensions of the first 72 and second 74 lateral sections of the bed top 56. In this embodiment, the lateral chambers 106, 108 are preferably completely independent of the main chamber 104. Also preferably, each chamber defines one or more baffles 110 that divides the chamber into zones. The zones may be independently inflated and/or deflated. The main chamber 104 is preferably positioned adjacent the main section 70 of the bed top 56 while the lateral chambers 106, 108 are preferably independently positioned adjacent the first 72 and second 74 lateral sections of the bed top. Furthermore, it is preferred that the lateral chambers 106, 108 are selectively attachable to the main chamber 104 of the patient support 58. Simple fasteners 112, such as hook and loop type fasteners and/or snap-like fasteners, can be used to facilitate the attachment of the lateral chambers 106, 108 to the main chamber 104. This arrangement allows easy removal of the lateral chambers 106, 108 of the patient support surface 58 when movement of the lateral sections 72, 74 of the bed top 56 away from the main section 70 is desired.

Alternatively, a foam or other compressible material can be used as the patient support 58. The trapped air of foam provides the preferred substantial radiotransparency. The foam may or may not be encased in a radiotransparent outer coating or cover, such as a carbon-fiber shell. In this embodiment, the foam is preferably divided into independent sections that correspond to the dimensions of the main 70 and lateral 72, 74 sections of the bed top 56, similar to that described above for the air mattress.

Figure 10:
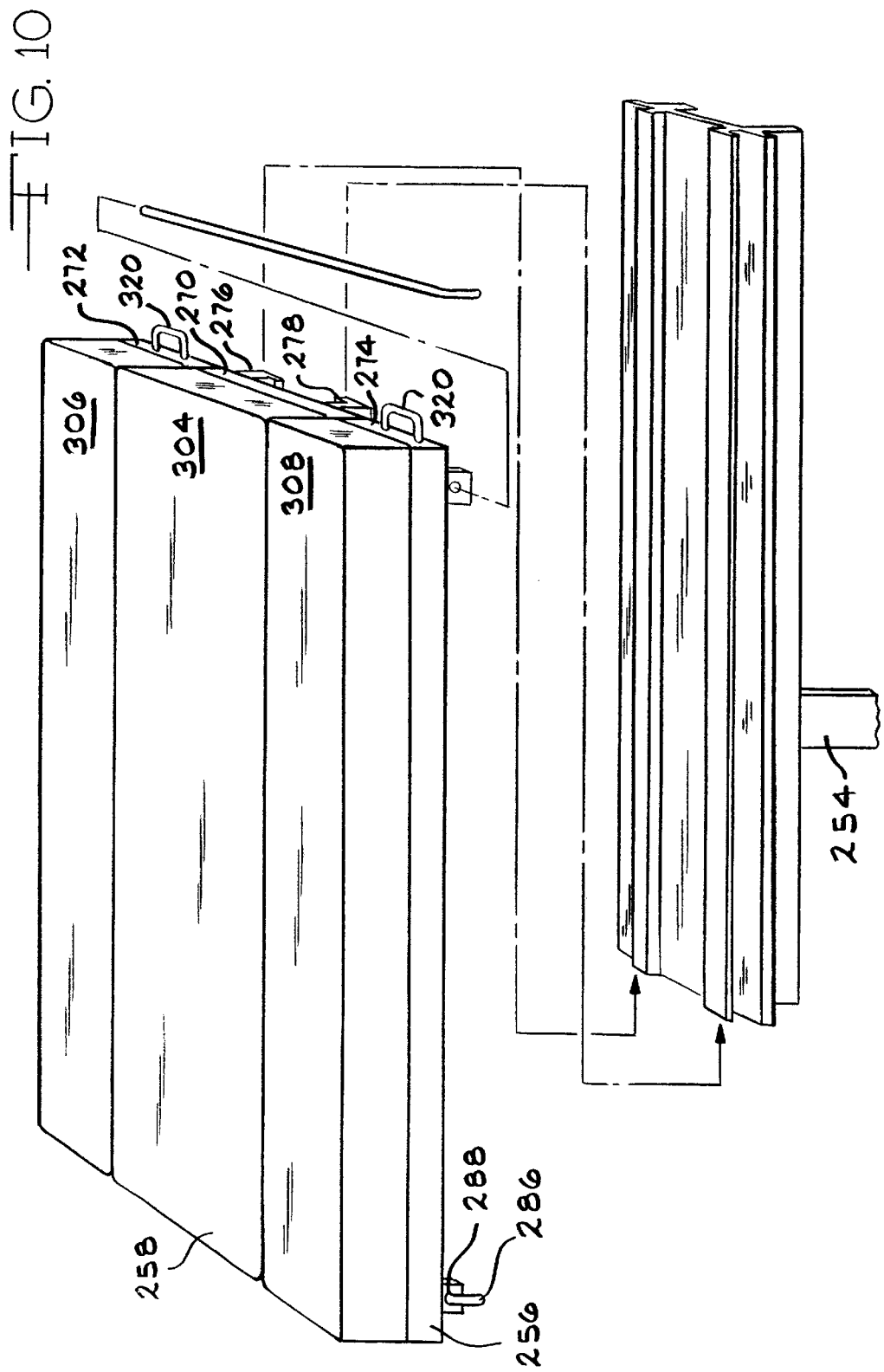
FIG. 10 is an exploded view of a patient support system in accordance with the present invention.

FIG. 10 illustrates a patient support system in accordance with an alternate embodiment of the present invention. The patient support system is similar to the hospital bed of the first preferred embodiment except as detailed below, and similar reference numbers refer to, similar components. In this embodiment, the bed top 256 and patient support surface 258 can be selectively and completely removed from the bed frame 254. This allows the bed top 256 and patient support surface 258 to serve as a support independent of the bed frame 254. In this embodiment, the bed top 256 and patient support 258 can serve as a stretcher, such as in a critical care vehicle, that can be attached to the bed frame 254 when appropriate.

Figure 11:
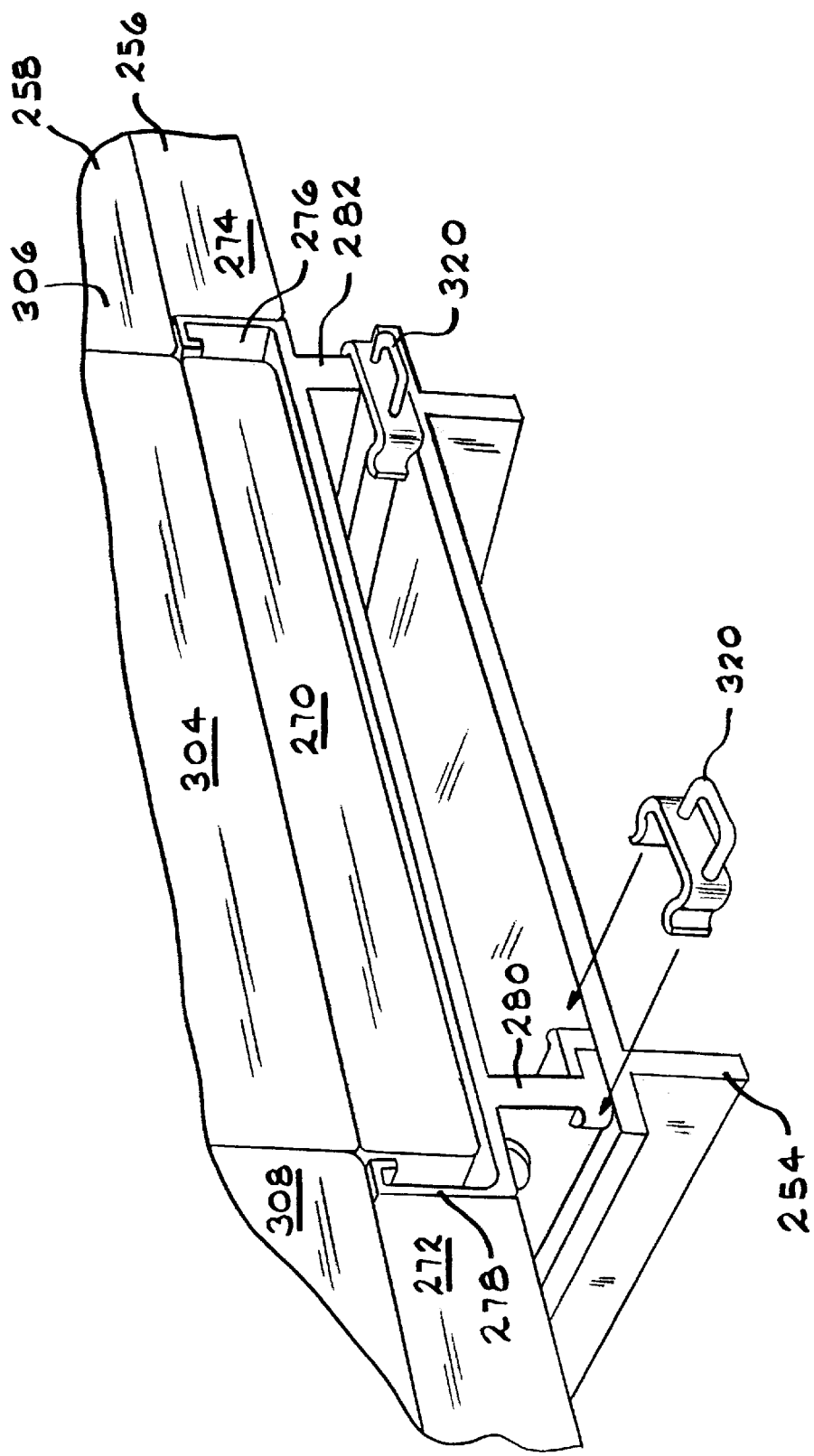
FIG. 11 is a magnified view of one end of the bed top and patient support surface of the patient support system illustrated in FIG. 10.

When attached to the bed frame 254, this embodiment retains the independence of the main 270 and lateral sections 272, 274 of the bed top 256 to the bed frame 254 as described above for the first preferred embodiment. This allows the axial displacement of the main section 270 and selective movement of the lateral sections 272, 274 when the bed top 256 is secured to the bed frame 254 as described above. To prevent the movement of these sections when the bed top 256 is detached from the bed frame 254, a locking connection is formed to fix the position of the main 270 and lateral sections 272, 274 relative to each other. The locking connection can be formed in a variety of manners. FIG. 10 illustrates an example of the locking connection. In this example, first and second rods or pins 286 extend through first and second complimentary channels or recesses 288 on the opposing ends of the bed top 256. One or more projections on the pin and complimentary recesses on the channel can be included such that the pin can be rotated, once fully inserted, into a locked position, thereby creating the locking connection As shown in FIG. 11, one or more retaining clips 320 are preferably included and serve to secure the bed top 256 of the patient support system to the bed frame 254 when appropriate. The retaining clips 320 preferably provide a secure connection between the two components while still allowing rapid detachment of the bed top 256 from the frame 254 when appropriate.

The references cited in this disclosure, except to the extent they may contradict any statements or definitions made herein, are hereby incorporated by reference in their entirety.

The foregoing disclosure is the best mode devised by the inventor for practicing the invention. It is apparent, however, that several variations in accordance with the present invention may be conceivable to one of ordinary skill in the relevant art. Inasmuch as the foregoing disclosure is intended to enable such person to practice the instant invention, it should not be construed to be limited thereby, but should be construed to include such aforementioned variations. As such, the present invention should be limited only by the spirit and scope of the following claims.

What is claimed is:

1. A hospital bed comprising a bed top having a main section and a section lateral with respect to the longitudinal axis of the main section, the main section being substantially radiotransparent and capable of independent axial displacement along the lengthwise axis of the bed top, and the lateral section being capable of selective movement away from the main section substantially along a lengthwise axis of the bed top.

2. A hospital bed in accordance with claim 1, further including means for indexing the axial displacement of the main section of the bed top such that the main section can be moved to any of a variety of predefined positions along the lengthwise axis of the bed top between the initial and extended positions.

3. A hospital bed in accordance with claim 1, wherein the bed top further comprises a second lateral section and wherein the main section is disposed between the first and second lateral sections when in an initial position.

4. A hospital bed in accordance with claim 1, further comprising a mobile base supporting the bed top.

5. A hospital bed comprising a bed top having a substantially radiotransparent main section disposed between first and second sections each lateral with respect to the longitudinal axis of the main section, the main section capable of independent axial displacement along the lengthwise axis of the bed top and at least one of the first and second lateral sections capable of selective movement away from the main section substantially along a lengthwise axis of the bed top.

\* \* \* \* \*